United States Patent [19]

Shroot et al.

[11] Patent Number: 5,173,289
[45] Date of Patent: Dec. 22, 1992

[54] AROMATIC ESTERS AND THIOESTERS, A PROCESS FOR THEIR PREPARATION AND THEIR USE IN HUMAN OR VETERINARY MEDICINE AND IN COSMETIC COMPOSITIONS

[75] Inventors: Braham Shroot, Antibes; Jacques Eustache, Grasse; Jean-Michel Bernardon, Nice, all of France

[73] Assignee: Centre International De Recherches Dermatologiques (C.I.R.D.), Valbonne, France

[21] Appl. No.: 480,486

[22] Filed: Feb. 16, 1990

Related U.S. Application Data

[63] Continuation-in-part of Ser. No. 298,982, Jan. 19, 1989, Pat. No. 4,925,658.

[51] Int. Cl.$^5$ .................... A61K 7/06; A61K 31/21; C07C 69/76
[52] U.S. Cl. ........................ 424/70; 514/513; 514/533; 514/544; 514/880; 560/59; 560/61
[58] Field of Search .............. 260/398.5; 560/59, 61, 560/102; 514/513, 533, 544, 880; 424/70

[56] References Cited

U.S. PATENT DOCUMENTS 3,979,360 9/1976 Spivak et al. ............... 260/398.5 X
4,051,104 9/1977 Spivak et al. ..................... 560/59 X

FOREIGN PATENT DOCUMENTS 0152097 8/1985 European Pat. Off. .
0309400 3/1989 European Pat. Off. .

*Primary Examiner*—Marianne M. Cintins
*Assistant Examiner*—Catherine S. Kilby Scalzo
*Attorney, Agent, or Firm*—Cushman, Darby & Cushman

[57] ABSTRACT

Aromatic esters and thioesters of the formula

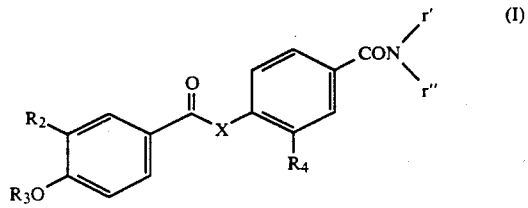

are useful in human and veterinary medicine and in cosmetic formulations. In the formula, X represents oxygen or sulfur, r' and 4" represent hydrogen, lower alkyl, monohydroxyalkyl, polyhydroxyalkyl, aryl or benzyl optionally substituted, the residue of an amino acid or aminated sugar, or taken together form a heterocycle, $R_2$ represents $\alpha$, $\alpha'$- dissubstituted alkyl having 4-12 carbon atoms or mono- or polycyclic cycloalkyl having 5-12 carbon atoms whose carbon linking carbon is trisubstituted and $R_3$ and $R_4$ represent hydrogen or lower alkyl.

8 Claims, No Drawings

AROMATIC ESTERS AND THIOESTERS, A PROCESS FOR THEIR PREPARATION AND THEIR USE IN HUMAN OR VETERINARY MEDICINE AND IN COSMETIC COMPOSITIONS

This is a continuation-in-part of application Ser. No. 07/298,982, filed Jan. 19, 1989, now U.S. Pat. No. 4,925,658.

BACKGROUND OF THE INVENTION

1. Field of the Invention

The present invention relates to new aromatic esters and thioesters, to a process for their preparation and to their use in human and veterinary medicine and in cosmetic compositions. These new aromatic esters and thioesters are usefully employed in the topical and systemic treatment of dermatologic ailments linked to a keratinization disorder (differentiation-proliferation) and dermatologic disorders, or others, having inflammatory and/or immunoallergic components and in conjunctive tissue degeneration illnesses. They also exhibit an antitumoral activity. Moreover, these derivatives can be used in the treatment of atopy, be it cutaneous or respiratory, and in the treatment of rheumatoid psoriasis.

The compounds of the present invention also find use in the ophthalmologic field and principally in the treatment of corneopathies.

The esters and thioesters, in accordance with the present invention, can be represented by the following formula:

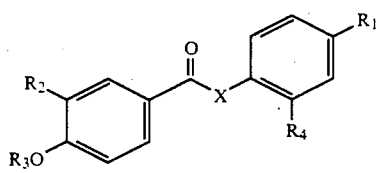

wherein
X represents oxygen or sulfur,
R represents —CH$_2$OH, —CH(OH)—CH$_3$, —COOR$_5$ or

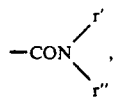

R$_5$ represents hydrogen, lower alkyl, lower alkenyl, monohydroxyalkyl or polyhydroxyalkyl,
r' and r'' represent hydrogen, lower alkyl, monohydroxyalkyl, polyhydroxyalkyl, aryl or benzyl optionally substituted, the residue of an amino acid or aminated sugar, or r' and r'' together with the nitrogen atom to which they are attached form a heterocycle,
R$_2$ represents α,α'-disubstituted alkyl having 4–12 carbon atoms or mono- or polycyclic cycloalkyl having 5–12 carbon atoms whose carbon linkage is trisubstituted,
R$_3$ represents hydrogen, lower alkyl, -Si(CH$_3$)$_2$R'$_3$ wherein R'$_3$ represents lower alkyl, and
R$_4$ represents hydrogen or lower alkyl, and
the salts of said aromatic esters and thioesters of formula (I) when R$_5$ represents hydrogen.

When the compounds in accordance with the present invention are provided in the form of salts, those preferred are the salts of an akali metal or an alkaline earth metal or a zinc salt or an organic amine salt.

By lower alkyl is meant a radical having 1–6 carbon atoms and principally methyl, ethyl, isopropyl, butyl and tert.butyl.

By α,α'disubstituted alkyl having 4–12 carbon atoms is meant principally a tert.butyl, 1,1-dimethylpropyl, 1-methyl-1-ethylpropyl, 1 methyl-1-ethylhexyl or 1,1-dimethyldecyl radical.

By monohydroxyalkyl is meant a radical having 2 or 3 carbon atoms and principally a 2-hydroxyethyl, 2-hydroxypropyl or 3-hydroxypropyl radical.

By polyhydroxyalkyl is meant a radical containing 3–6 carbon atoms and 2–5 hydroxyl groups, such as 2,3-dihydroxypropyl, 2,3,4-trihydroxybutyl, 2,3,4,5-tetrahydroxypentyl or the residue of pentaerythritol.

By aryl is meant phenyl or phenyl substituted by halogen, hydroxy or nitro.

By mono- or polycyclic cycloalkyl having 5–12 carbon atoms whose carbon linkage is trisubstituted is meant 1-methylcyclohexyl or 1-adamantyl.

By amino acid residue is meant a residue derived, for example, from lysine or glycine.

By residue of an aminated sugar is meant a residue derived, for example, from glucosamine, galactosamine or mannosamine.

When the r' and R'' radicals taken together form a heterocycle, the heterocycle preferably is a piperidino, piperazino, morpholino, pyrrolidino or 4-(2-hydroxyl ethyl) piperazino heterocycle.

Representative compounds of formula (I) above include principally the following:

4-[3-(1-adamantyl)-4-methoxybenzoyloxy]benzoic acid,
4-[3-(1-adamantyl)-4-methoxybenzoylthio]benzoic acid,
4-[3-(1-methylcyclohexyl)-4-methoxybenzoyloxy]benzoic acid,
4-[3-(1-methylcyclohexyl)-4-benzoylthio]benzoic acid,
4-[3-(1,1-dimethyldecyl)-4-methoxybenzoyloxy]benzoic acid,
4-[3-(1,1-dimethyldecyl)-4-methoxybenzoylthio]benzoic acid,
4-[3-(1-adamantyl)-4-hydroxybenzoyloxy]benzoic acid,
4-[3-(1-adamantyl)-4-hydroxybenzoylthio]benzoic acid,
ethyl 4-[3-(1-adamantyl)-4-ethyl 4-methoxybenzoyloxy]benzoate,
ethyl 4-[3 -(1-adamantyl)-4-methoxybenzoylthio]benzoate,
N-ethyl 4-[3-(1-adamantyl)-4-methoxybenzoyloxy]benzamide,
the morpholide of 4-[3-(I-adamantyl)-4-methoxybenzoylthio]benzoic acid,
allyl 4-[3-(1-adamantyl)-4-methoxybenzoyloxy]benzoate,
4-[3-tert.butyl-4-methoxybenzoylthio]benzoic acid,
methyl 4-[3-(1-adamantyl)-4-methoxybenzoylthio]benzoate,
N-ethyl 4-[3-(1-adamantyl)-4-methoxybenzoylthio]benzamide,
2-hydroxyethyl 4-[3-(1-adamantyl)-4-methoxybenzoylthio]benzoate,
4-[3-(1-adamantyl)-4-t.ert.butyldimethyl-silyloxybenzoylthio]benzoic acid,
allyl 4-[3-(1-adamantyl)-4-hydroxybenzoyloxy]benzoate, 3-methyl 4-[3-(1-adamantyl)-4-methoxybenzoyloxy]-benzoic acid, 4-[3-(1-adamantyl)-4-methoxybenzoyloxy]benzoic aldehyde, 4-[3-(1-adamantyl)-4-methoxybenzoyloxy]benzyl alcohol.

4-[3-(1-adamatyl)-4-methoxybenzoylthio]benzamide,

4-[3-(1-adamantyl)-4-methoxybenzoyloxy]benzamide,

N,N-dimethyl,4-[3-(1-adamantyl)4-methoxybenzoyloxy]benzamide and, 3-tert.butyl-4-[3-(1-adamantyl)-4-methoxybenzoyloxy]-benzoic acid.

The present invention also relates to a process for preparing the compounds of formula (I) in accordance with the following reaction scheme:

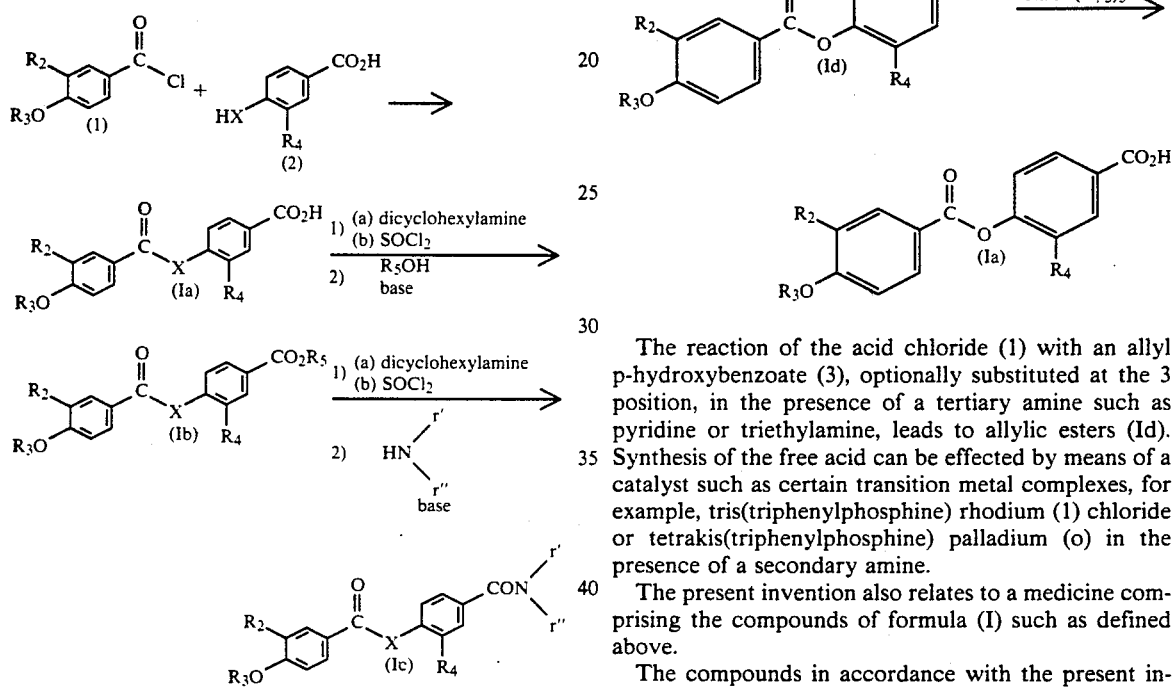

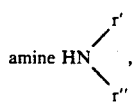

gives the corresponding ester (Ib) or amide (Ic).

The compounds of formula (Ia) in which X represents oxygen can also be prepared in accordance with the following reaction scheme:

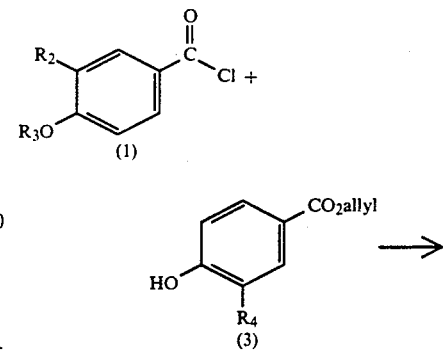

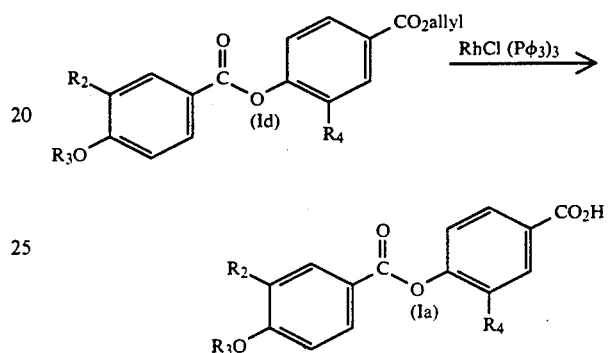

The principal step of this preparation comprises reacting, in an anhydrous medium, in an organic solvent such as tetrahydrofuran or methylene chloride containing a tertiary amine (pyridine or triethylamine), an activated form of a substituted benzoic acid, for example, an acid chloride (1), or a mixed anhydride, with a p-hydroxy or p-thio benzoic acid, optionally substituted in position 3 (2), the reaction being carried out at ambient temperature with stirring.

The (Ia) acids thus obtained can be converted in a known manner into a corresponding acid chloride which, when treated with an alcohol (R5OH) or an The reaction of the acid chloride (1) with an allyl p-hydroxybenzoate (3), optionally substituted at the 3 position, in the presence of a tertiary amine such as pyridine or triethylamine, leads to allylic esters (Id). Synthesis of the free acid can be effected by means of a catalyst such as certain transition metal complexes, for example, tris(triphenylphosphine) rhodium (1) chloride or tetrakis(triphenylphosphine) palladium (o) in the presence of a secondary amine.

The present invention also relates to a medicine comprising the compounds of formula (I) such as defined above.

The compounds in accordance with the present invention exhibit good stability to light and oxygen.

The compounds of the present invention exhibit excellent activity in the inhibition test of ornithine decarboxylase in nude rats, after induction, by "tape stripping", M. Bouclier et al., Dermatologica, 169, No.4, 1984. This test is recognized as a measure of the inhibiting activity of certain compounds on cellular proliferation phenomena.

The compounds of the present invention are particularly active in the differentiation test of embryonic tetracarcinoma cells of mice (F9 cells) (Cancer Research 43, p.5268, 1983).

Finally, the new compounds are characterized by the introduction in the chemical structure of an ester or thioester linkage which is highly sensitive to the action of various esterases in vivo, which leads to the rapid inactivation of molecules by conversion into biologically inactive fragments.

The compounds of the present invention are indeed particularly suitable in the following treatment fields:

(1) for the treatment of dermatologic ailments linked to keratinization disorder causing differentiation and proliferation and principally for the treatment of acne vuloaris. comedons, polymorphs, nodulokystic acne, conglobata, senile acne, secondary acne such as solar acne, medicinal acne or professional acne;

(2) for the treatment of other types of keratinization disorders and principally ichtysoses, ichthyosiform conditions, Darier malady, palmoplantary keratodermies, leucoplasies and leucoplasiform conditions and lichen;

(3) for the treatment of dermatologic ailments linked to a keratinization disorder having an inflammatory and/or immunoallergic component and principally, all forms of psoriasis, be they cutaneous, mucous or ungual, and even psoriasic rheumatism, or again cutaneous atopies, such as eczema, or respiratory atopies; the compounds can also be used in certain inflammatory ailments not exhibiting any keratinization disorder;

(4) for the treatment of all dermic or epidermic proliferations that are benign or malignant, that are either of viral origin such as common warts, plane warts and epidermodysplasie verruciform, the proliferation being able to be induced by ultraviolet radiations, principally in the case of baso epithelioma and cellular spino;

(5) for the treatment of other dermatologic disorders such as blistery dermatoses and collagen maladies;

(6) for the treatment of ophthalmologic disorders, and principally for the treatment of corneopathies;

(7) for combatting against ageing of the skin, be it photoinduced or not; and (8) to prevent or heal scars of epidermic or dermic atoPies. induced by local or systemic corticosteroids, or any other form of cutaneous atophy.

The present invention also relates to medicinal compositions containing at least one compound of formula (I), such as defined above, or one of its salts.

The present invention thus relates to a new mecidical composition, intended principally for the treatment of the ailments mentioned above, comprising in a pharmaceutically acceptable support at least one compound of formula (I) and/or one of its salts.

The compounds according to the present invention are generally administered to a human or animal host at a daily dosage of about 0.01 mg/kg to 100 mg/kg of body weight.

As the vehicle or support for these compositions any conventional vehicle can be employed, the active component being found either in the dissolved state, or in the dispersed state, in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotions, gels, sprays or suspensions.

These topically applied compositions can be provided in anhydrous form or in aqueous form, according to clinical indications.

When administered ocularly, the medicinal composition is principally in the form of an eyewash.

The compounds of formula I, according to the present invention, are also useful in the cosmetic field, and in particular in body and hair hygiene compositions and principally for the treatment of skin having acne tendencies, to improve the growth of hair, i.e., to promote the growth of existing hair follicles, to combat hair loss, to combat against an oily appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula I or one of its salts, this composition being provided principally in the form of a lotion, gel, soap or shampoo.

The concentration of the compound of formula I in these cosmetic compositions is between 0.0001 and 0.1 percent by weight and preferably between 0.001 and 0.01 percent by weight, based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, S-benzylcysteamine, their salts and their derivatives, tioxolone or benzoylperoxide; antibiotics such as erythromycin and its esters, neomycin, tetracyclines or 4,5-polymethylene-3-isothiazolinones; agents promoting the growth of hair, such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidine dione); steroidal and non-steroidal anti-inflammatory agents; carotenoids and, principally, $\beta$-carotene; anti-psoriasic agents such as anthralin and its derivatives and 5,8,11,14-eicosatetraynoic and 5,8,11-eicosatriynoic acids, and their esters and amides.

The compositions according to the present invention can also include flavor improving agents, preservatives, stabilizers, humidity regulating agents, pH regulating agents, osmotic pressure modifying agents, emulsifiers, UV-A and UV-B filters, and antioxidants such as $\alpha$-tocopherol, butylhydroxyanisole or butylhydroxytoluene.

The following non-limiting examples illustrate the preparation of the active compounds of formula I according to the present invention as well as compositions containing these compounds.

Examples of Preparation

EXAMPLE 1

Preparation of allyl 4-[3-(1-adamantyl)-4-methoxybenzoyloxy]benzoate 2.86 g (10 mmoles) of 3-(1-adamantyl)-4-methoxybenzoic acid, described in French Patent No. 85 13747 (2.570.377) in Example 26, and 10 ml of thionyl chloride (SOCl$_2$) are heated to reflux up to the cessation of gaseous emission. The reaction mixture is evaporated to dryness, taken up by 20 ml of tetrahydrofuran (THF) and the solution thus obtained is slowly added to a solution of allyl p-hydroxybenzoate (1.78 g, 10 mmoles) and triethylamine (1.5 ml, 11 mmoles), in THF (50 ml).

The reaction mixture is stirred for 4 hours at 20° C., poured into water, extracted with ether and dried over magnesium sulfate.

The solvents are evaporated and the residue is chromatographed on a silica column (eluant: 1/1 mixture of CH$_2$Cl$_2$/hexane). 3.0 g (68% yield) of the expected product having a melting point of 109°-110° C. are obtained.

EXAMPLE 2

Preparation of 4-[3-(1-adamantyl)-4-methoxybenzoyloxy]benzoic acid 2.8 g (6.2 mmoles) of the ester prepared in Example I are dissolved in 100 ml of a 9/1 mixture of ethanol and water. 75 mg of a tris(triphenyl-phosphine) rhodium chloride complex are added and the reaction mixture is heated at reflux for 12 hours. The reaction mixture is cooled and the solids are filtered and then dissolved in a 9/1 mixture of dichloromethane and THF. The reaction mixture is washed with water, dried (MgSO$_4$) and the solvents are evaporated.

The solid is taken up in 50 ml of ethylether to give 1 g (40% yield) of 4-[3-(1-adamantyl)-4-methoxybenzoyloxy]benzoic acid having a melting point of 265°-267° C.

EXAMPLE 3

Preparation of 4-[3-(1-adamantyl)-4-methoxybenzoylthio]benzoic acid

In a round bottom flask, there are introduced 1.7 g (11 mmoles) of 4-mercaptobenzoic acid and 20 ml of pyridine. There is then slowly added a solution of 3.4 g (11.17 mmoles) of 3-(1-adamantyl)-4-methoxybenzoic acid chloride in 50 ml of dichloromethane. The reaction mixture is stirred at ambient temperature for 8 hours, evaporated to dryness, taken up in 100 ml of water and acidified to pH 5 with 1N HCl. The solid is filtered, washed with water and dried at 60° C. under a vacuum, then recrystallized in dioxan. 3.3 g (75% yield) of 4-[3-(1-adamantyl)-4-methoxybenzoylthio]benzoic acid having a melting point of 264° C. are obtained.

EXAMPLE 4

Preparation of 4-[3-(1-methylcyclohexyl)-4-methoxybenzoylthio]benzoic acid (a) 4-bromo-2-(1-methylcyclohexyl) phenol.

In a round bottom flask, there are introduced 11.42 g (100 mmoles) of 1-methylcyclohexanol, 50 ml of heptane and 270 µl of concentrated sulfuric acid.

There are then slowly added 10.8 ml (117 mmoles) of acetic anhydride and the reaction mixture is stirred at ambient temperature for 18 hours. 2.7 ml (50 mmoles) of concentrated sulfuric acid are then added and in small portions 17.3 g (100 mmoles) of 4-bromophenol. The reaction mixture is stirred at ambient temperature for 24 hours, evaporated to dryness and taken up in 200 ml of water. The pH is adjusted to 7 with sodium bicarbonate and extracted with ethylether. The organic phase is decanted, dried over magnesium sulfate and evaporated. The residue is purified by chromatography on a silica column by using as the eluant a 40/60 mixture of dichloromethane and hexane. The solvents are evaporated and 8.97 g (33% yield) of 4-bromo-2-(1-methylcyclohexyl) phenol in the form of a yellowish oil are obtained.

(b) 4-bromo-2-(1-methylcyclohexyl) anisole

The 4-bromo-2-(1-methyloyclohexyl) phenol (9.26 g, 34.4 mmoles) is dissolved in 50 ml of THF. The solution is cooled to 0° C. and in small portions 1.14 g (37.8 mmoles) of sodium hydride (80% in oil) are added. The reaction mixture is stirred for 30 minutes at ambient temperature and 5.37 g (37.8 mmoles) of methyl iodide are slowly added thereto. Stirring is continued for 16 hours and 300 ml of water are added. The reaction mixture is then extracted with ethylether (3×300 ml). The organic phase is decanted and washed with a saturated solution of sodium bicarbonate, then with a saturated solution of sodium chloride.

The reaction mixture is dried (Mg SO$_2$), filtered and the solvents are evaporated. The residue is purified by chromatography on a silica column, eluted by a 20/80 mixture composed of dichloromethane and hexane. 9 g (92% yield) of 4-bromo-2-(1-methylcyclohexyl) anisole in the form of a colorless oil are obtained.

(c) 3-(1-methylcyclohexyl)-4-methoxybenzoic acid

The compound obtained in step 4(b), above, (9 g, 31.8 mmoles) is dissolved in 50 ml of dry THF. The resulting solution is slowly added over magnesium (850 mg, 35 mmoles) and an iodide crystal. After introduction of the first 5 milliliters, the reaction mixture is heated at reflux and maintained at this condition for 15 minutes after the addition is terminated. The reaction mixture is cooled to −40° C. and a current of CO$_2$ is passed therethrough for one hour. The reaction mixture is then poured into 6N HCl and extracted with ethyl ether (3×300 ml). The organic phase is decanted, washed with water until neutral, dried (Mg SCO$_4$), and evaporated. The resulting residue is ground in hexane, filtered and dried. 6.50 g (82% yield) of 3-(1-methylcyclohexyl)-4-methoxybenzoic acid having a melting point of 199° C. are obtained.

(d) 3-(1-methylcyclohexyl)-4-methoxybenzoic acid chloride 1.24 g (5 mmoles) of 3-(1-methylcyclohexyl)-4-methoxybenzoic acid and 15 ml of thionyl chloride are heated at reflux until the cessation of gas evolution. The reaction mixture is evaporated to dryness. 1.32 g (100% yield) of crude 3-(1-methylcyclohexyl)-4-methoxybenzoic acid chloride which is used as such for the following synthesis are obtained.

(e) 4-[3-(1-methylcyclohexyl)-4-methoxy-benzoylthio]benzoic acid.

In a round bottom flask, there are introduced 771 mg (5 mmoles) of 4-mercaptobenzoic acid and 8 ml of pyridine. A solution of 1.32 mg (5 mmoles) of the acid chloride obtained in step 4(d) above dissolved in 20 ml of dichloromethane is slowly added. The reaction mixture is stirred at ambient temperature for 5 hours. It is then evaporated to dryness, taken up in water, acidified to pH 5 with 1N HCl and extracted with ethyl ether (500 ml). The organic phase is decanted, dried over magnesium sulfate and evaporated to dryness. The resulting residue is purified by chromatography on a silica column, eluted by an 80/20 mixture composed of dichloromethane and ethyl ether. 1.55 g (81% yield) of 4-[3-(1-methylcyclohexyl)-4-methoxybenzoylthio]benzoic acid having a melting point of 216°-218° C. are obtained.

EXAMPLE 5

Preparation of 4-[3-(1,1-dimethyldecyl)-4-methoxybenzoylthio]benzoic acid

Crude 3-(1,1-dimethyldecyl)-4-methoxybenzoic acid, prepared starting with 1.6 g (5 mmoles) of 3-(1,1-dimethyldecyl)-4-methoxybenzoic acid, described in Example 11 of European Patent No. 0.232.199 is dissolved in 20 ml of dichloromethane. The solution is slowly added to a mixture of 771 mg (5 mmoles) of 4-mercaptobenzoic acid and 8 ml of pyridine. The reaction mixture is stirred at ambient temperature for 8 hours, evaporated to dryness, taken up in water, acidified to pH 5 with 1N HCl and extracted with ethyl ether (500 ml). The organic phase is decanted, washed with water, dried over magnesium sulfate and evaporated to dryness. The resulting residue is purified by chromatography on a silica column, by using as the eluant ethyl ether. 1.92 g (84% yield) of 4-[3-(1,1-dimethyldecyl)-4-methoxybenzoylthio]benzoic acid whose melting point is 186°-187° C. are obtained.

EXAMPLE 6

Preparation of 4-[3-tert.butyl-4-methoxybenzoylthio]benzoic acid.

Crude 3-(tert.butyl)-4-methoxybenzoic acid, prepared starting with 1.04 g (5 mmoles) of 3-(tert.butyl)-4-methoxybenzoic acid, described in Example 35 of French Patent No. 85 13747 (2.570.377), is dissolved in 15 ml of dichloromethane. The solution is slowly added to a mixture of 771 mg (5 mmoles) of 4-mercaptobenzoic acid and 8 ml of pyridine. The reaction mixture is stirred at ambient temperature for 8 hours, evaporated to dryness, taken up in water, acidified to pH 5 with 1N HCl and extracted with ethyl ether. The organic phase is decanted, washed with water, dried over magnesium sulfate and evaporated to dryness. The resulting residue is purified by chromatography on a silica column (eluant: ethyl ether). The solvent is evaporated and 530 mg (32% yield) of 4-[3-tert.butyl-4-methoxybenzoylthio]benzoic acid whose melting point is 220°-221° C. are obtained.

EXAMPLE 7

Preparation of methyl 4-[3-(1-adamantyl)-4-methoxybenzoylthio]benzoate (a) 4-[3-(1-adamantyl)-4-methoxybenzoylthio]benzoic acid chloride.

Into a round bottom flask there are introduced 3.80 g (9 mmoles) of 4-[3-(1-adamantyl)-4-methoxybenzoylthio]benzoic acid, 40 ml of dichloromethane and 1.8 ml (9 mmoles) of dicyclohexylamine. The reaction mixture is stirred for one hour. To the resulting solution 720 µl (9.9 mmoles) of thionylchloride are added and the mixture is stirred at ambient temperature for 2 hours. It is then evaporated to dryness, and taken up in 500 ml of ethyl ether. The dicyclohexylammonium chloride is filtered and the solvent is evaporated. 3.97 g (100% yield) of crude 4-[3-(1-adamantyl)-4-methoxybenzoylthio]benzoic acid chloride which is used as such for the following synthesis are obtained.

(b) methyl 4-[3-(1-adamantyl)-4-methoxybenzoylthio]benzoate

A solution of 1.28 g (2.9 mmoles) of the acid chloride obtained in step 7(a), above, in 30 ml of THF is slowly added to a mixture of 240 µl (5.8 mmoles) of methyl alcohol and 404 µl (2.9 mmoles) of triethylamine in 20 ml of THF. The mixture is stirred for 8 hours and then poured into water and extracted with ethyl ether (500 ml). The organic phase is decanted, washed with water, dried over magnesium sulfate and then evaporated. The resulting residue is purified by chromatography on a silica column, eluted with a 40/60 mixture of dichloromethane and hexane. The solvents are evaporated and 890 mg (70% yield) of the expected ester having a melting point of 138°-140° C. are obtained.

EXAMPLE 8

Preparation of N-ethyl 4-[3-(1-adamantyl)-4-methoxybenzoylthio]benzamide

A solution of 1.28 g (2.9 mmoles) of the acid chloride obtained in Example 7(a) in 30 ml of THF is slowly added to a solution of 395 µl (5.8 mmoles) of ethylamine in 20 ml of THF. The mixture is stirred for 4 hours then poured into water and extracted with ethyl ether (500 ml). The organic phase in decanted, washed with water, dried on magnesium sulfate and evaporated. The resulting residue is purified by chromatography on a silica column, eluted with a 20/80 mixture of ethyl ether and dichloromethane. The solvents are evaporated and 820 mg (61% yield) of the expected amide whose melting point is 185°-186° C. are obtained.

EXAMPLE 9

Preparation of the morpholide of 4-[3-(1-adamantyl)-4-methoxybenzoylthio]benzoic acid A solution of 1.28 g (2.9 mmoles) of the acid chloride obtained in Example 7(a) in 30 ml of THF is slowly added to a mixture of 510 µl (5.8 mmoles) of morpholine in 30 ml of THF. The mixture is stirred for 16 hours, then poured into water and extracted with ethyl ether (800 ml). The organic phase is decanted, washed with water, dried over magnesium sulfate and evaporated to dryness. The resulting residue is ground in 30 ml of ethyl ether, filtered and dried. 960 mg (68% yield) of the amide whose melting point is 178°-180° C. are recovered.

EXAMPLE 10

Preparation of 2-hydroxyethyl 4-[3-(1-adamantyl)-4-methoxybenzoylthio]benzoate

A solution of 1.28 g (2.9 mmoles) of the acid chloride obtained in Example 7(a) in 30 ml of THF is slowly added to a mixture of 1.62 ml (29 mmoles) of ethyleneglycol and 235 µl (2.9 mmoles) of pyridine in 20 ml of THF. The mixture is stirred for 16 hours, then poured into water and extracted with ethyl ether (500 ml). The organic phase is decanted, washed with water, dried over magnesium sulfate and evaporated. The resulting residue is recrystallized in an 80/20 mixture of isopropylether and cyclohexane. 783 mg (58% yield) of the expected ester whose melting point is 115°-117° C. are recovered.

EXAMPLE 11

Preparation of 4-[3-(1-adamantyl)-4 tert.butyldimethylsilyloxybenzoylthio]benzoic acid The crude 3-(1-adamantyl)-4-tert.butyl-dimethylsilyloxybenzoic acid, prepared starting with 3.8 g (9.95 mmoles) of the corresponding acid, described in Example 3 of European Patent No. 0.232.199, is dissolved in 40 ml of dichloromethane. The solution is slowly added to a mixture of 1.54 g (9.95 mmoles) of 4-mercaptobenzoic acid and 15 ml of pyridine. The reaction mixture is stirred at ambient temperature for 12 hours, evaporated to dryness, taken up in water and acidified to pH 5 with 1N HCl. The solid is filtered, washed with water, ground with 50 ml of ethyl ether and dried at 60° C. under a vacuum. 5 g (96% yield) of a white powder whose melting point is 232°–233° C. are recovered.

EXAMPLE 12

Preparation of 4-[3-(1-adamantyl)-4-hydroxybenzoylthio]benzoic acid

Into a round bottom flask there are introduced 3.66 g (7 mmoles) of the acid obtained in Example 11 and 50 ml of THF. 7.7 ml (7.7 mmoles) of tetrabutylammonium fluoride (1M in THF) are slowly added and the mixture is stirred at ambient temperature for one hour. The reaction mixture is poured into water and extracted with dichloromethane. The organic phase is decanted and dried over magnesium sulfate. The solvents are evaporated and the resulting solid is ground in 100 ml of ethyl acetate at reflux, cooled and filtered. 1.28 g (45% yield) of 4-[3-(1-adamantyl)-4-hydroxybenzoylthio]benzoic acid whose melting point is 272°–274° C. are obtained.

EXAMPLE 13

Preparation of allyl 4-[3-(1-adamantyl)-4-hydroxybenzoyloxy]benzoate (a) allyl 4-[3-(1-adamantyl)-4-tert.butyldimethylsilyloxybenzoyloxy]benzoate Crude 3-(1-adamantyl)-4-tert.butyldimethylsilyloxybenzoic acid chloride prepared starting with 3.7 g (9.6 mmoles) of the corresponding acid, is dissolved in 35 ml of THF. The solution is slowly added to a mixture of 1.72 g (9.6 mmoles) of allyl 4-hydroxybenzoate, 1.5 ml (10.6 mmoles) of triethylamine and 25 ml of THF. The reaction mixture is stirred at ambient temperature for 12 hours, and then poured into water and extracted with ethyl ether. The organic phase is decanted, washed with water, dried over magnesium sulfate and evaporated. The resulting residue is purified by chromatography on a silica column by using as the eluant a 50/50 mixture of dichloromethane and hexane. 3.96 g (75% yield) of the allyl ester whose melting point is 118°–120° C. are thus recovered.

(b) allyl 4-[3-(1-adamantyl)-4-hydroxybenzoyloxy]benzoate

Into a round bottom flask there are introduced 3.91 g (7.15 mmoles) of t,he,.allyl ester obtained in step 13(a), above, and 50 ml of THF. 7.9 ml (7.9 mmoles) of tetrabutylammonium fluoride (1M in THF) are slowly added and the reaction mixture is stirred at ambient temperature for 2 hours. The reaction mixture is poured into water and extracted with dichloromethane. The organic phase is decanted, dried over magnesium sulfate and evaporated. The resulting residue is purified by chromatography on a silica column, eluted by an 80/20 mixture of dichloromethane and hexane. After evaporation of the solvents, 2.88 g (93% yield) of allyl 4-[3-(1-adamantyl)-4-hydroxybenzoyloxy]benzoate whose melting point is 175°–177° C. are obtained.

EXAMPLE 14

Preparation of 4-[3-(1-adamantyl)-4-hydroxybenzoyloxy]benzoic acid

Into a round bottom flask there are introduced 2.16 g (5 mmoles) of the ester obtained in Example 13(b) and 30 ml of THF. Under a stream of nitrogen, 290 mg of tetrakis(triphenylphosphine) palladium (0) are added and then 4.35 ml (50 mmoles) of morpholine are slowly introduced. The reaction mixture is stirred at ambient temperature for two hours and evaporated to dryness. The residue is ground in ether and the resulting solid is filtered. The solid is then introduced into 100 ml of water, acidified to pH 1 and extracted With 800 ml of ethyl ether. The organic phase is decanted, washed with water, dried over magnesium sulfate and evaporated. The residue is ground in 50 ml of ethyl ether, filtered and dried. 1.05 g (54% yield) of the expected acid whose melting point is 269°–271° C. are obtained.

EXAMPLE 15

Preparation of 3-methyl-4-[3-(1-adamantyl)-4-methoxybenzoyloxy]-benzoic acid.

(a) allyl 4-hydroxy-3-methylbenzoate

Into a round bottom flask there are introduced 9.5 g (62 mmoles) of 4-hydroxy-3-methylbenzoic acid and 70 ml of allyl alcohol. 1.8 ml of concentrated sulfuric acid are added and the mixture is heated at 100° C. for 8 hours. The reaction mixture is then evaporated to dryness, neutralized with sodium bicarbonate and extracted with dichloromethane. The organic phase is decanted, washed with water, dried over magnesium sulfate and evaporated. The resulting residue is purified simply by filtration over silica (eluant: dichloromethane). After evaporation of the solvents, 8.76 g (92% yield) of the expected ester whose melting point is obtained.

(b) allyl 3-methyl-4-[3-(1-adamantyl)-4-methoxybenzoyloxy]-benzoate

Into a round bottom flask, there are introduced 1.92 g (10 mmoles) of the ester obtained in step 15(a), 1.5 ml (11 mmoles) of triethylamine and 50 ml of THF. A solution of 3.04 g (10 mmoles) of 3-(1-adamantyl)-4-methoxybenzoic acid chloride in 20 ml of THF is slowly added and the mixture is stirred for 24 hours at ambient temperature. The reaction mixture is then poured into water and extracted with ethyl ether. The organic phase is decanted, washed initially with bicarbonated water and then with water, dried over magnesium sulfate and evaporated. The resulting residue is purified by chromatography on a silica column by eluting with a 50/50 mixture of dichloromethane and hexane. 3 g (65% yield) of allyl 3-methyl-4-[3-(1-adamantyl)-4-methoxybenzoyloxy]benzoate having a melting point of 138°–139° C. are recovered.

(c) 3-methyl-4-[3-(1-adamantyl)-4-methoxybenzoyloxy]-benzoic acid 2.35 g (5 mmoles) of the ester prepared in step 15 (b) above are dissolved in 50 ml of THF. Under a stream of nitrogen, 78.3 mg of tetrakis(triphenylphosphine) palladium (0) are added and then 4.4 ml (50 mmoles) of morpholine are slowly introduced. The reaction mixture is then stirred at ambient temperature for 2 hours and evaporated to dryness. The residue is ground in ethyl ether and the solid is filtered. The solid is then introduced into 10 ml of water, acidified to pH 1, extracted with a 3/1 mixture of ethyl ether and THF. The organic phase is decanted, washed with water, dried over magnesium sulfate and evaporated. The residue is ground in 50 ml of ethyl ether, filtered and dried. 1.6 g (70% yield) 277° C. are obtained.

EXAMPLE 16

Preparation of - 4-[3-(1-adamantyl)-4-methoxybenzoyloxy]benzoic aldehyde

Into a round bottom flask there are introduced 1.22 g (10 mmoles) of 4-hydroxybenzaldehyde, 1.53 ml (II mmoles) of triethylamine and 50 ml of THF. A solution of 3.04 g (10 mmoles) of 3-(1-adamantyl)-4-methoxybenzoic acid chloride in 20 ml of THF is slowly added and the reaction mixture is stirred for 18 hours at ambient temperature. The reaction mixture is then poured into water and extracted with ethyl ether. The organic phase is decanted, washed with water, dried over magnesium sulfate and evaporated. The resulting residue is purified by chromatography on a silica column, eluted with 4 g (62% yield) of the aldehyde whose melting point is 243°-245° C. are obtained.

EXAMPLE 17

Preparation of 4-[3-(1-adamantyl) 4-methoxybenzoyloxy]benzyl alcohol 2.1 g (5.4 mmoles) of the aldehyde obtained in Example 16 are dissolved in 30 ml of methanol and treated with 310 mg (8.2 mmoles) of sodium borohydride. The mixture is stirred at ambient temperature for 2 hours, poured into water and extracted with ethyl ether. The organic phase is decanted, washed with water, dried over magnesium sulfate and evaporated. The resulting residue is purified by chromatography on a silica column by using as the eluant a 90/10 mixture of dichloromethane and ethyl ether. 1.45 g (68% yield) of the expected alcohol whose melting point is 168°-169° C. are recovered.

EXAMPLE 18

Preparation of 3-tert.butyl-4-[3-(1-adamantyl)-4-methoxybenzoyloxy]- benzoic acid (a) allyl 4-hydroxy-3-tert.butylbenzoate Into a round bottom flask, there are introduced 9.71 g (50 mmoles) of 4-hydroxy-3-tert.butyl benzoic acid and 55 ml of allyl alcohol. 1.3 ml of concentrated sulfuric acid are added and the mixture in heated at 100° C. for 18 hours. The reaction mixture is then evaporated to dryness and 200 ml of water are added. The mixture is then neutralized with sodium bicarbonate and extracted with ethyl ether. The organic phase is decanted, washed with water, dried over magnesium sulfate and evaporated. The resulting residue is purified by chromatography on a silica column by eluting with dichloromethane. After evaporation of the solvents, 9.78 g (83% yield) of the expected ester whose melting point is 131°-132° C. are obtained.

(b) allyl 3-tert.butyl-4-[3-(1-adamantyl)-4-methoxybenzoyloxy]- benzoate

Into a round bottom flask, there are introduced 2.34 g (10 mmoles) of the ester obtained in step 18(a), above, 1.53 ml (11 mmoles) of triethylamine and 30 ml of THF. A solution of 3.04 g (IO mmoles) of 3-(1-adamantyl)-4-methoxybenzoic acid chloride in 20 ml of THF is slowly added and the reaction mixture is stirred for 24 hours at ambient temperature. The reaction mixture is then poured into water and extracted with ethyl ether. The organic phase is decanted, washed initially with bicarbonated water and then with water, dried over magnesium sulfate and evaporated. The resulting residue is purified by chromatography on a silica column by eluting with a 40/60 mixture of dichloromethane and hexane. 2.8 g (56% yield) of allyl 3-tert.butyl-4-[3-(1-adamantyl)-4-methoxybenzoyloxy]benzoate having a melting point of 113°-115° C. are thus recovered.

(c) 3-tert.butyl-4-[3-(1-adamantyl)-4-methoxybenzoyloxy]- benzoic acid 2.51 g (5 mmoles) of the ester prepared in step 18(b) above are dissolved in 25 ml of THF. Under a stream of nitrogen 145 mg of tetrakis(triphenylphosphine) palladium (O) are added. Then slowly there are introduced 4.4 ml (50 mmoles) of morpholine. The mixture is stirred at ambient temperature for one hour and evaporated to dryness. The residue is taken up in ethyl ether and the morpholine salt formed is filtered. This salt is then introduced into 100 ml of water, acidified to pH 1 with concentrated HCl and extracted with ethyl ether. The organic phase is decanted, washed with water, dried over magnesium sulfate and evaporated. The residue is taken up in 50 ml of ethyl ether, filtered and dried. 1.6 g (70% yield) of the expected acid having a melting point of 260°-262° C. are obtained.

EXAMPLE 19

Preparation of 4-[3-(1-adamantyl)-4)-methoxybenzolythio]benzamide (a) 4-[3-(adamantyl)-4-methoxybenzoylthio]benzoic acid chloride.

3.80 g (9 mmoles) of 4-[3-(1-adamantyl)-4)-methoxybenzolythio]benzoic acid, 40 ml of dichloromethane, 1.8 ml (9 mmoles) of dicyclohexylamine are introduced into a round bottomed flask and are stirred for one hour. To the solution thus produced, are added 720 82 1 (9.9 mmoles) of thionyl chloride and this is stirred at ambient temperature for two hours. This is then evaporated to dryness, taken up in 500 ml of ethyl ether, followed by filtering the dicyclohexylammonium chloride and then by evaporating the solvent. By this means are obtained 3.97 g (100% ) of crude 4-[3-(1-adamantyl)-4)-methoxybenzolythio]benzoic acid chloride which is used directly for the later synthesis.

(b) 4-[3-(1-adamantyl)-4)-methoxybenzolythio]benzamide

Into a solution of 4.4 g (10 mmoles) of the acid chloride obtained in example 19(a) in 30 ml of tetrahydrofocan (THF) are introduced, while cooling to −20° C., 450 mg (26 mmoles) of ammonia. The mixture is stirred for four hours at ambient temperature and is then poured into water and extracted with ethyl ether (500 ml). The organic phase is decanted, washed in water, dried on magnesium sulphate and evaporated. The residue obtained is purified by chromatography over a silica column and eluted with a mixture of THF and dichlormethane (10/90). The solvents are evaporated and 1.5 g (36%) of amide is obtained having a melting point of 244°–248° C.

EXAMPLE 20

Preparation of 4-[3-(1-adamantyl)-4)-methoxybenzolyoxy]benzamide 200 mg (0.48 mmoles) of 4-[3-(1-adamantyl)-4)-methoxybenzoloxy]benzoic acid, 10 ml of toluene and 0.01 ml of dimethylformamide are introduced into a three necked round bottomed flask in an atmosphere of nitrogen. While stirring, the mixture is heated to 50° C. and thionyl chloride is added dropwise. The mixture is then heated to 70°–75° C. for one and a half hours. The disappearance of the starting product is established by thin layer chromotography (TLC) using a methanol-dichloromethane (10/90) system. Thereafter the mixture is cooled and maintained at mabient temperature. Then 0.1 ml of 35% ammonia is added dropwise to the clear reaction mixture which is stirred. The precipitate thus produced is filtered in a sintered funnel, washed with distilled water until neutral and dried in a ventilated oven at 80° C. for one night. This yields 100 mg (50%) of amide having a metling point of 255°–257° C.

EXAMPLE 21

Preparation of N,N-dimethyl 4-[3-(1-adamantyl)-4)-methoxybenzoloxy benzamide 1.35 g (3 mmoles) of 4-[3-(1-adamantyl)-4)-methoxybenzoloxy]benzoic acid, 13 ml of toluene and 0.07 ml of dimethylformamide are introduced into a three necked round bottomed flask under an atmosphere of nitrogen. While stirring and heating to 50° C., 0.29 ml (4 mmoles) of thionyl chloride is added drop by drop. Then the mixture is heated to 70°–75° C. for an hour and a half. The disappearance of the starting reactant is determined by TLC using a methanol-dichloromethane (10/90) system followed byc ooling and maintaining at ambient temperature. Next, 3.8 ml of dimethylamine diluted to 40% in water are added drop by drop to the clear reaction mixture which is then stirred for 30 minutes. The white precipitate thus obtained is filtered in a sintered funnel, washed with distilled water until neutral and dried in a ventilated oven at 80° C. for one night. This yields 1.15 g (79%) of amide having a melting point of 215°–218° C.

EXAMPLE 22

Preparation of N-ethyl 4-[3-(1-adamantyl)-4)-methoxybenzoloxy]benzamide 2.03 g (5 mmoles) of 4-[3-(1-adamantyl)-4)-methoxybenzolyoxy]benzoic acid, 20 ml of toluene and 0.1 ml of dimethylformamide are introduced into a three necked round bottomed flask in an atmosphere of nitrogen. While stirring and heating to 50° C., 0.45 ml (6 mmoles) of thionyl chloride is added to the mixture drop by drop. Heating is then carried out at 70°–75° C. for one and a half hours. The disappearance of the starting reagent is established by TLC using a methanol-dichloromethane (10/90) system followed by cooling and maintaining at ambient temperature. Next, 5.5 ml of ethylamine diluted to 12.6% in water are added drop by drop to the clear reaction mixture which is thereafter stirred for 30 minutes. The white precipitate thus obtained is filtered in a sintered funnel, washed with distilled water until neutral and dried in a ventilated overn at 80° C. for one night. This yields 1.44 g (66%) of amide having a melting ponit of 164°–166° C.

Examples of Compositions

| A. Oral Compositions | |
|---|---|
| (a) 0.2 g tablet | |
| 4-[3-(1-adamantyl)-4-methoxy-benzoylthio] benzoic acid | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampoules | |
| 4-[3-(1-adamantyl)-4-methoxy-benzoyloxy] benzoic acid | 0.001 g |
| Glycerine | 0.500 g |
| Sorbitol, 70% | 0.500 g |
| Sodium saccharinate | 0.010 g |
| Methyl p-hydroxybenzoate | 0.040 g |
| Flavor, sufficient amount | |
| Purified water, sufficient amount | 5 ml |
| (c) 0.8 g tablet | |
| 4-[3-(1-adamantyl)-4-methoxy-benzoyloxy] benzoic acid | 0.500 g |
| Pregelatinized starch | 0.100 g |
| Microcrystalline cellulose | 0.115 g |
| Lactose | 0.075 g |
| Magnesium stearate | 0.010 g |

In Example (c), above the 4-[3-(1-adamantyl)-4)-methoxybenzolyoxy]benzoic acid can be replaced by 3-methyl-4-[3-(1-adamantyl)-4-methoxybenzoyloxy]-benzoic acid.

| (d) Drinkable suspension in 10 ml ampoules | |
|---|---|
| 4-[3-(1-adamantyl)-4-methoxy-benzoyloxy] benzoic acid | 0.200 g |
| Glycerine | 1.000 g |
| Sorbitol, 70% | 1.000 g |
| Sodium saccharinate | 0.010 g |
| Methyl p-hydroxybenzoate | 0.080 g |
| Flavor, sufficient amount | |
| Purified water, sufficient amount for | 10.000 ml |

In Example (d), above the 4-[3-(1-adamantyl)-4)-methoxybenzolyoxy ]benzoic acid can be replaced by the same amount of the morpholide of 4-[3-(1-adamantyl)-4)-methoxybenzolthio]benzoic acid.

| B. Topical Compositions | |
|---|---|
| (a) Ointment | |
| 4-[3-(1-adamantyl)-4-methoxy-benzoylthio] benzoic acid | 0.020 g |
| Isopropyl myristate | 81.700 g |
| Liquid petrolatum oil | 9.100 g |
| Silica, sold by Degussa under the tradename "Aerosil 200" | 9.180 g |
| (b) Ointment | |
| 4-[3-(1-methylcyclohexyl)-4-methoxy-benzoylthio] benzoic acid | 0.300 g |
| White petrolatum, codex, sufficient amount for | 100.000 g |

In Example (b), above, the 4-[3-(1-methylcylohexyl)-4-methoxybenzoylthio]benzoic acid can be replaced by the same amount of 4-[3-(1-adamantyl)-4)-methoxybenzolthio]benzoic acid or 2-hydroxyethyl 4-[3-(1-adamantyl)-4-methoxybenzoylthio]benzoate.

| (c) Non-ionic water-in-oil cream | |
|---|---|
| 4-[3-(1-adamantyl)-4-hydroxy-benzoyloxy] benzoic acid | 0.100 g |
| Anhydrous eucerin | 39.900 g |
| Methyl p-hydroxybenzoate | 0.075 g |
| Propyl p-hydroxybenzoate | 0.075 g |
| Sterile demineralized water, sufficient amount for | 100.00 g |

In Example (c), above, the 4-[3-(1-adamantyl)-4-hydroxybenzoyloxy]benzoic acid can be replaced by the same amount of 4-[3-(1-adamantyl)-4-methoxybenzoylthio]benzoic acid.

| (d) Anionic oil-in-water cream | |
|---|---|
| 4-[3-(1-methylcyclohexyl)-4-methoxybenzoylthio] benzoic acid | 1.000 g |
| Sodium dodecyl sulfate | 0.772 g |
| 1,2-propanediol | 1.540 g |
| Cetyl alcohol | 19.300 g |
| Thick petrolatum oil | 19.300 g |
| Methyl p-hydroxybenzoate | 0.075 g |
| Propyl p-hydroxybenzoate | 0.075 g |
| Sterile demineralized water, sufficient amount for | 100.000 g |

In Example (d), above, the 4-[3-(1-methylcylohexyl)-4-methoxybenzoylthio]benzoic acid can be replaced by the same amount of 4-[3-(1-adamantyl)-4)-methoxybenzolthio ]benzoic acid.

| (e) Lotion | |
|---|---|
| 4-[3-(1-adamantyl)-4-hydroxy-benzoyloxy] benzoic acid | 0.100 g |
| PEG 400 | 69.900 g |
| Ethanol, 95% | 30.000 g |

In Example (e), above, the 4-[3-(1-methylcylohexyl)-4-methoxybenzoylthio]benzoic acid can be replaced by the same amount of 4-[3-(1-adamantyl)-4)-methoxybenzolthio ]benzoic acid.

| (f) Ethanolic gel | |
|---|---|
| 4-[3-(1-methylcyclohexyl)-4-methoxybenzoylthio] benzoic acid | 0.300 g |
| Hydroxypropyl cellulose | 2.000 g |
| Ethanol, 95%, sufficient amount for | 100.000 g |
| (g) Hydrophobic ointment | |
| Methyl 4-[3-(1-adamantyl)-4-methoxybenzoylthio] benzoate | 0.300 g |
| Isopropyl myristate | 36.400 g |
| Silicone oil, sold under the tradename "Rhodorsil 47V300" by Rhone-Poulenc | 36.400 g |
| Beeswax | 13.600 g |
| Silicone oil, sold under the tradename "Abil 300.000 cst" by Goldschmidt, sufficient amount for | 100.000 g |
| (h) Aqueous gel | |
| 4-[3-(1-adamantyl)-4-methoxy-benzoylthio] benzoic acid | 0.300 g |
| Poloxamer 162 | 0.200 g |
| Propylene glycol | 4.000 g |

| -continued | |
|---|---|
| Polymer of acrylic acid, sold under the tradename "Carbopol 940" by Goodrich | 0.800 g |
| Disodium EDTA | 0.100 g |
| Methyl p-hydroxybenzoate | 0.100 g |
| NaOH, 10% in water | 1.250 g |
| Sterile demineralized water, sufficient amount for | 100.000 g |

In Example (h), above, the 4-[3-(1-methylcylohexyl)-4-methoxybenzoylthio]benzoic acid can be replaced by the same amount of 4-[3-(1-adamantyl)-4)-methoxybenzolthio ]benzoic acid.

| (i) Anhydrous gel | |
|---|---|
| 4-[3-(1-adamantyl)-4-methoxy-benzoyloxy] benzoic acid | 0.100 g |
| Silica, sold under the tradename "Aerosil 200" by Degussa | 7.000 g |
| Isopropyl myristate, sufficient amount for | 100.000 g |
| (j) Non-ionic oil-in-water cream | |
| 4-[3-(1-adamantyl)-4-methoxy-benzoyloxy] benzoic acid | 1.000 g |
| Cetyl alcohol | 4.000 g |
| Glycerol monostearate | 2.500 g |
| PEG 50 stearate | 2.500 g |
| Karite butter | 9.200 g |
| Propylene glycol | 2.000 g |
| Methyl p-hydroxybenzoate | 0.075 g |
| Propyl p-hydroxybenzoate | 0.075 g |
| Sterile demineralized water, sufficient amount for | 100.000 g |
| (k) Flexible film | |
| 4-[3-(1-adamantyl)-4-methoxy-benzoylthio] benzoic acid | 0.100 g |
| Silicone elastomer, sold under the tradename "Rhodorsil RTV141A" by Rhone-Poulenc | 89.900 g |
| Cold catalyst, sold under the tradename "RTV 141B" by Rhone-Poulenc | 10.000 g |
| C. Injectable Composition | |
| Injectable ampoule for intravenous administration | |
| Micronized 4-[3-(1-adamantyl)-4-hydroxybenzoyloxy] benzoic acid | 0.003 |
| Water for injectable preparation, sufficient amount for | 3 ml |

In the immediately preceding Example, the 4-[3-(1-adamantyl)-4-hydroxybenzoyloxy]benzoic acid can be replaced by the same amount of 4-[3-(1-adamantyl)-4)hydroxybenzoylthio]benzoic acid.

What is claimed is:

1. A pharmaceutical composition comprising in a pharamceutically acceptable vehicle, for enteral, parenteral, topical or ocular administration to a human or animal, a therapeutically effective amount of at least one compound of formula (I)

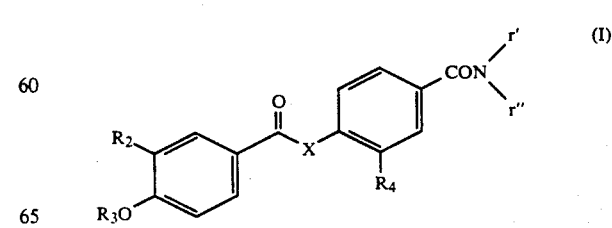

wherein
X represents oxygen, r' and r", each independently, represent hydrogen, lower alkyl, monohydroxyalkyl, polyhydroxyalkyl, phenyl, phenyl substituted by halogen, hydroxyl or nitro, benzyl or benzyl substituted by halogen, hydroxy or nitro, $R_2$ represents $\alpha,\alpha'$-disubstituted alkyl having from 4–12 carbon atoms and selected from the group consisting of a tert. butyl, 1,1-dimethylpropyl, 1-methyl-1-ethylpropyl, 1-methyl-1-ethylhexyl and 1,1-dimethyl decyl radical, 1-methylcyclohexyl or 1-adamantyl, and $R_3$ and $R_4$, each independently, represent hydrogen or lower alkyl.

2. The pharmaceutical composition of claim 1 wherein said compound of formula (I) is selected from the group consisting of
N-ethyl 4-[3-(1-adamantyl)-4-methoxybenzoyloxy]benzamide,
4-[3-(1-adamantyl)-4-methoxybenzoyloxy]benzamide and
N,N-dimethyl 4-[3-(1-adamantyl)-4-methoxy benzoyloxy]benzamide.

3. The pharmaceutical composition of claim 1 wherein said compound of formula (I) is present in an amount ranging from 0.0001 to about 5 percent by weight based on he total weight of said composition.

4. A process for the treatment of dermatologic, rheumatismal, respiratory or ophthalmologic ailments comprising administering to a human or animal a therapeutically effective amount of the pharmaceutical composition of claim 1.

5. A cosmetic composition for body and hair hygiene comprising in a cosmetically acceptable vehicle a cosmetically effective amount of at least one compound of formula (I):

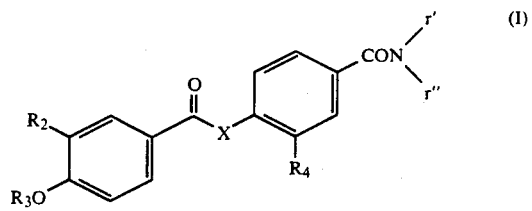

wherein
r' and r", each independently, represent hydrogen, lower alkyl, monohydroxyalkyl, polyhydroxyalkyl, phenyl, phenyl substituted by halogen, hydroxyl or nitro, benzyl or benzyl substituted by halogen, hydroxy or nitro, $R_2$ represents $\alpha,\alpha'$-disubstituted alkyl having from 4–12 carbon atoms and selected from the group consisting of tert.butyl, 1,1-dimethylpropyl, 1-methyl-1-ethylpropyl, 1-methyl-1-ethylhexyl and 1,1-dimethyl decyl radical, 1-methylcyclohexyl or 1-adamantyl, and $R_3$ and $R_4$, each independently, represent hydrogen or lower alkyl.

6. The cosmetic composition of claim 5 wherein said compound of formula (I) is selected from the group consisting of
N-ethyl 4-[3-(1-adamantyl)-4-methoxybenzoyloxy]benzamide,
4-[3-(1-adamantyl)-4-methoxybenzoyloxy]benzamide and
N,N-dimethyl 4-[3-(1-adamantyl)-4-methoxy benzoyloxy]benzamide.

7. The cosmetic composition of claim 5 wherien said compound of formula (I) is present in an amount ranging from 0.0001 to 0.1 percent by weight based on the total weight of said composition.

8. The cosmetic composition of claim 5 wherien said compound of formula (I) is present in an amount ranging from 0.0001 to 0.1 percent by weight based on the total weight of said composition.

* * * * *